(12) United States Patent
Laokroekkiat et al.

(10) Patent No.: US 12,239,955 B2
(45) Date of Patent: Mar. 4, 2025

(54) PROCESS FOR REMOVING ARSINE FROM HYDROCARBON MIXTURE

(71) Applicant: PTT Global Chemical Public Company Limited, Bangkok (TH)

(72) Inventors: Salinthip Laokroekkiat, Bangkok (TH); Sitthiphong Pengpanich, Bangkok (TH); Kaew-Arpha Thavornprasert, Bangkok (TH)

(73) Assignee: PTT Global Chemical Public Company Limited, Chatuchak Bangkok (TH)

( * ) Notice: Subject to any disclaimer, the term of this patent is extended or adjusted under 35 U.S.C. 154(b) by 130 days.

(21) Appl. No.: 17/911,990

(22) PCT Filed: Mar. 12, 2021

(86) PCT No.: PCT/IB2021/052066
§ 371 (c)(1),
(2) Date: Sep. 15, 2022

(87) PCT Pub. No.: WO2021/186307
PCT Pub. Date: Sep. 23, 2021

(65) Prior Publication Data
US 2023/0125196 A1    Apr. 27, 2023

(30) Foreign Application Priority Data

Mar. 18, 2020   (TH) ............................... 2001001557

(51) Int. Cl.
*B01J 20/22*      (2006.01)
*B01D 53/02*      (2006.01)
(Continued)

(52) U.S. Cl.
CPC ............ *B01J 20/226* (2013.01); *B01D 53/02* (2013.01); *B01J 20/3085* (2013.01); *C07C 7/12* (2013.01);
(Continued)

(58) Field of Classification Search
CPC ..... B01J 20/226; B01J 20/3085; B01D 53/02; B01D 2253/204; B01D 2256/24; B01D 2257/553; C07C 7/12
See application file for complete search history.

(56) References Cited

U.S. PATENT DOCUMENTS

| 4,933,159 A | 6/1990 | Nowack et al. |
| 4,962,272 A | 10/1990 | Cullo et al. |

(Continued)

FOREIGN PATENT DOCUMENTS

WO   2019090071 A1   5/2019

OTHER PUBLICATIONS

Wikipedia 'MOF-5' Mar. 31, 2019 (Mar. 31, 2019) retrieved from <https://en.wikipedia.org/w/index.php?title=MOF-5&oldid=890227059> entirety of document especially p. 1 para 1.
(Continued)

*Primary Examiner* — Youngsul Jeong
(74) *Attorney, Agent, or Firm* — Troutman Pepper Locke LLP

(57) ABSTRACT

The present invention relates to a process for removing arsine from hydrocarbon mixture having 2 to 4 carbon atoms. Said process comprises the contact of the hydrocarbon mixture having 2 to 4 carbon atoms with the adsorbent, wherein said adsorbent is the metal organic frameworks (MOFs) comprising:
 a) at least 1 transition metal selected from group 1B metal, group 2B metal, and group 4B metal, and
 b) the organic ligand selected from dicarboxylic acid compound or tricarboxylic acid compound,
(Continued)

and wherein said adsorbent is subjected to the treatment with alcohol.

13 Claims, 1 Drawing Sheet

(51) Int. Cl.
    *B01J 20/30*      (2006.01)
    *C07C 7/12*      (2006.01)

(52) U.S. Cl.
    CPC .... *B01D 2253/204* (2013.01); *B01D 2256/24* (2013.01); *B01D 2257/553* (2013.01)

(56) References Cited

U.S. PATENT DOCUMENTS

| | | | |
|---|---|---|---|
| 6,960,700 B1 | 11/2005 | Sethna et al. | |
| 2014/0058088 A1* | 2/2014 | Rende | C07C 2/76 564/204 |
| 2015/0034500 A1* | 2/2015 | Kim | B01J 20/28016 423/406 |
| 2015/0308623 A1 | 10/2015 | Li et al. | |
| 2018/0236434 A1 | 8/2018 | Vityuk et al. | |

OTHER PUBLICATIONS

International Search Report and Written Opinion issued in International Application No. PCT/IB2021/052066 dated Jun. 11, 2021.

\* cited by examiner

PROCESS FOR REMOVING ARSINE FROM HYDROCARBON MIXTURE

This application is a U.S. national stage application of International Application No. PCT/IB2021/052066, filed on Mar. 12, 2021, which claims priority from Thailand application No. 2001001557, filed Mar. 18, 2020. The entire contents of each application are hereby incorporated by reference in their entirety.

TECHNICAL FIELD

The present invention relates to the field of chemistry, in particular, to the process for separating compound using porous adsorbent.

BACKGROUND ART

The removal of arsenic compounds from olefins which are ethylene and propylene in the production process is a necessary process in order to avoid causing toxicity to the catalyst. The separation and removal of arsenic compounds from hydrocarbon stream in the production process is performed by adsorption method considering from the type of origin, type of arsenic compound wanted to be removed, and conditions used in the removal. From said information, it can be used to design suitable adsorbent for such arsenic compound. The arsenic compound mostly found is arsine because it is volatile and stable and has the boiling point that is close to that of propylene.

The metal oxide adsorbents for removing arsine compounds have been basically described. Patent document U.S. Pat. No. 6,960,700B1 discloses the synthesis and the use of metal oxide of copper on alumina support having 7 to 10% by weight of copper to adsorb the arsine compounds in hydrocarbon stream. Although the adsorbent of copper oxide on support has been widely used, there is limitation in usage since it can be only used for removing arsine compounds from hydrocarbon stream having no reactive compounds such as acetylene, methylacetylene-propadiene (MAPD), and diene etc. This is because the copper metal may produce acetylide salts when reacting with acetylene compound under thermal condition; moreover, acetylene compound can react with each other using metal oxide of copper as the catalyst, causing polymerization that produces unwanted products such as green oil or cuprene.

Patent document U.S. Pat. No. 4,962,272A discloses the synthesis and use of metal oxide of lead on alumina support having 18 to 24% by weight of metal oxide of lead on the support to adsorb arsine compounds in hydrocarbon stream, including the reuse process of said adsorbent by passing oxygen-free heated inert gas having moisture content of 1 to 15%. However, the use of metal oxide of lead may cause harm to human health and environment. Therefore, the efficient disposal system of used adsorbent is needed. Moreover, the metal oxide of lead has lower arsine compounds adsorption ability than the adsorbent having copper component at the same adsorbent amount.

Patent document U.S. Pat. No. 4,933,159A discloses the synthesis and the use of silver metal, silver nitrate compound, and/or metal oxide of silver on the supports which are alumina, alumina fluoride, silica, silica fluoride, titanium oxide, and/or magnesium aluminate to remove arsine compounds, especially trialkyl arsine compounds in which alkyl group has 1-6 carbon atoms. Said adsorbent has 2 to 15% by weight of silver metal. However, the hydrocarbon stream is flown through the mixed metal oxide adsorbent of copper and zinc prior to contact with the above adsorbent bed having silver component.

Patent document US20180236434A and WO2019090071A disclose the synthesis and the use of metal oxide of bismuth on the supports which are alumina, titanium oxide, silicon oxide, cerium oxide, zirconium oxide, magnesium oxide, zeolite, and/or activated carbon to remove arsine compounds in hydrocarbon stream. Said adsorbent has 2 to 50% by weight of bismuth and has lead content of 5% by weight as efficiency enhancer.

There has been reported that the active component loading on the porous support not only can increase the dispersion of the active component, but also increases the contact surface area in the reaction or the adsorption. This leads to the increase in adsorption ability. The adsorbents normally used are alumina, silica, zeolite, and activated carbon. However, there is limitation of the contact surface area in terms of porosity and ability of characteristic tuning of the support.

The metal organic frameworks (MOFs) are one of porous materials that gains interest in the usage in the adsorption process because it has outstanding adsorption/desorption characteristics. Many of them have functional groups that cause the specific adsorption and increase the bonding. Moreover, some of them have high contact surface area and porosity, including porosity having more orderliness compared to other porous materials. This causes the metal organic frameworks to have the important specific property, that is the ability to design and synthesize them to be suitable for the industrial applications. From all above, this invention aims to improve the separation process of arsine from hydrocarbon mixture having 2 to 4 carbon atoms using the metal organic frameworks (MOFs) having high adsorption ability.

SUMMARY OF INVENTION

The present invention relates to a process for removing arsine from hydrocarbon mixture having 2 to 4 carbon atoms. Said process comprises the contact of the hydrocarbon mixture having 2 to 4 carbon atoms with the adsorbent, wherein said adsorbent is the metal organic frameworks (MOFs) comprising:
  a) at least 1 transition metal selected from group 1B metal, group 2B metal, and group 4B metal, and
  b) the organic ligand selected from dicarboxylic acid compound or tricarboxylic acid compound,
  and wherein said adsorbent is subjected to the treatment with alcohol.

DESCRIPTION OF THE INVENTION

Figure 1:
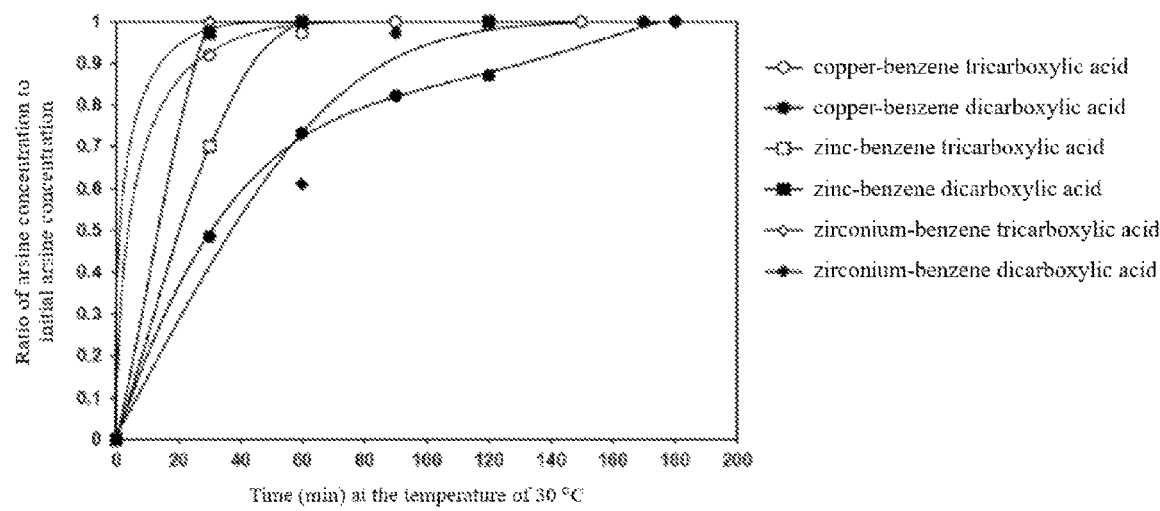
FIG. 1 shows the arsine separation performance of the metal organic frameworks prepared using different transition metal ions and organic ligands at the mole ratio of transition metal to organic ligand of 2:1.

The present invention relates to the process for removing arsine from hydrocarbon mixture having 2 to 4 carbon atoms, which will be described in the following aspects of the invention.

Any aspect being described herein also means to include the application to other aspects of this invention unless stated otherwise.

Technical terms or scientific terms used herein have definitions as understood by an ordinary person skilled in the art unless stated otherwise.

Any tools, equipment, methods, or chemicals named herein mean tools, equipment, methods, or chemicals being operated or used commonly by those person skilled in the art unless stated otherwise that they are tools, equipment, methods, or chemicals specific only in this invention.

Use of singular noun or singular pronoun with "comprising" in claims or specification means "one" and also including "one or more", "at least one", and "one or more than one".

All compositions and/or methods disclosed and claims in this application are intended to cover embodiments from any operation, performance, modification, or adjustment any factors without any experiment that significantly different from this invention, and obtain with object with utility and resulted as same as the present embodiment according to person ordinary skilled in the art although without specifically stated in claims. Therefore, substitutable or similar object to the present embodiment, including any minor modification or adjustment that can be apparent to person skilled in the art should be construed as remains in spirit, scope, and concept of invention as appeared in appended claims.

Throughout this application, term "about" means any number that appeared or expressed herein that could be varied or deviated from any error of equipment, method, or personal using said equipment or method.

Hereafter, invention embodiments are shown without any purpose to limit any scope of the invention.

The present invention relates to the process for removing arsine from hydrocarbon mixture having 2 to 4 carbon atoms. Said process comprises the contact of the hydrocarbon mixture having 2 to 4 carbon atoms with the adsorbent, wherein said adsorbent is the metal organic frameworks (MOFs) comprising:
 a) at least 1 transition metal selected from group 1B metal, group 2B metal, and group 4B metal, and
 b) the organic ligand selected from dicarboxylic acid compound or tricarboxylic acid compound, and wherein said adsorbent is subjected to the treatment with alcohol.

In one aspect of the invention, group 1B metal is selected from copper and silver.

In one aspect of the invention, group 2B metal is selected from zinc.

In one aspect of the invention, group 4B metal is selected from titanium and zirconium.

Preferably, the metal organic frameworks comprise the transition metals which are copper, zinc, and zirconium, most preferably copper.

In one aspect of the invention, the organic ligand is selected from 1,4-benzene dicarboxylic acid, 1,3,5-benzene tricarboxylic acid, 2,6-naphthalene dicarboxylic acid, and 1,2,4,5-benzene tetracarboxylic acid, preferably 1,3,5-benzene tricarboxylic acid.

In one aspect of the invention, the mole ratio of the transition metal to the organic ligand is in the range of about 1:1 to 3:1, more preferably about 2:1.

In one aspect of the invention, alcohol is selected from methanol, ethanol, propanol, and butanol, preferably methanol.

In one aspect of the invention, the adsorbent treatment with alcohol is performed by contacting with alcohol in the amount of 2 to 5 mole of alcohol per gram of the adsorbent weight.

In one aspect of the invention, the hydrocarbon having 2 to 4 carbon atoms is selected from ethane, propane, propylene, n-butane, and isobutane, preferably propane and propylene.

In one aspect of the invention, the contact of hydrocarbon mixture having 2 to 4 carbon atoms with the adsorbent according to the invention is operated at the temperature in the range of 25 to 40° C. and the pressure in the range of atmospheric pressure to about 3,000 kPa, preferably temperature in the range of 30 to 40° C. and the pressure in the range of about 100 to 500 kPa, and most preferably at the atmospheric pressure.

The gas hourly space velocity (GHSV) of the feed line of the hydrocarbon in the adsorption is in the range of about 3,400 to 37,000 mL $h^{-1}$ adsorbent weight$^{-1}$, preferably in the range of 15,000 to 30,000 mL $h^{-1}$ adsorbent weight$^{-1}$.

Generally, person skilled in this art can adjust the adsorption conditions to be suitable for types and compositions of the hydrocarbon mixture, adsorbent, and column system.

In one aspect, the process for removing arsine in which the contact of hydrocarbon mixture having 2 to 4 carbon atoms with the adsorbent according to the invention may be operated in continuous fixed-bed adsorption column or batch adsorption system.

In another aspect of the invention, the metal organic frameworks according to the invention may be prepared by the following steps:
 a) preparing the solution comprising the mixture comprising at least 1 transition metal selected from group 1B metal, group 2B metal, and group 4B metal, and the organic ligand selected from dicarboxylic acid compound or tricarboxylic acid compound,
 b) subjecting the mixture obtained from step a) to solvothermal process at determined temperature and time in order to produce the metal organic frameworks, and
 c) subjecting the material obtained from step b) to treatment with alcohol at determined temperature and time.

In one aspect of the invention, step b) and c) may further comprise the drying which may be performed by conventional drying method using oven, vacuum drying, stirred evaporation, and drying by rotary evaporator.

The following examples are only for demonstrating one aspect of this invention, not for limiting the scope of this invention in any way.

Preparation of the Adsorbent

Copper-Benzene Tricarboxylic Acid Adsorbent 1,3,5-benzene tricarboxylic acid solution and copper nitrate trihydrate ($Cu(NO_3)_2 \cdot 3H_2O$) solution in dimethylformamide solvent were prepared with determined mole ratio. Then, said copper nitrate trihydrate solution was added into 1,3,5-benzene tricarboxylic acid solution and the mixture was stirred up. After that, said mixture was transferred into autoclave in order to perform the solvothermal process at the temperature about 100° C. for about 24 hours. When the solvothermal process was completed, the solution was cooled down to room temperature. Then, said mixture was filtered and washed with dimethylformamide. The obtained solid was dried at the temperature about 160° C. in the oven under reduced pressure for 24 hours. The metal organic frameworks were obtained.

Copper-Benzene Dicarboxylic Acid Adsorbent

The sample was prepared by the method described for the copper-benzene tricarboxylic acid adsorbent using 1,4-benzene dicarboxylic acid instead of 1,3,5-benzene tricarboxylic acid.

Zinc-Benzene Tricarboxylic Acid Adsorbent 1,3,5-benzene tricarboxylic acid solution in dimethylformamide solvent and zinc nitrate hexahydrate ($Zn(NO_3)_2 \cdot 6H_2O$) solution in dimethylformamide solvent were prepared. Then, said zinc nitrate hexahydrate solution was added into 1,3,5-benzene tricarboxylic acid solution and the mixture was stirred up. After that, said mixture was transferred into autoclave in order to perform the solvothermal process at the temperature about 100° C. for about 24 hours. When the solvothermal process was completed, the solution was cooled down to room temperature. Then, said mixture was filtered and washed with dimethylformamide. The obtained solid was dried at the temperature about 160° C. in the oven under reduced pressure for 24 hours. The metal organic frameworks were obtained.

Zinc-Benzene Dicarboxylic Acid Adsorbent

The sample was prepared by the method described for the zinc-benzene tricarboxylic acid adsorbent using 1,4-benzene dicarboxylic acid instead of 1,3,5-benzene tricarboxylic acid.

Zirconium-Benzene Tricarboxylic Acid Adsorbent 1,3,5-benzene tricarboxylic acid solution in dimethylformamide solvent and zirconium oxide chloride octahydrate ($ZrOCl_2 \cdot 8H_2O$) solution in dimethylformamide solvent and formic acid were prepared. Then, said zirconium oxide chloride octahydrate solution was added into 1,3,5-benzene tricarboxylic acid solution and the mixture was stirred up. After that, said mixture was transferred into autoclave in order to perform the solvothermal process at the temperature about 120° C. for about 48 hours. When the solvothermal process was completed, the solution was cooled down to room temperature. Then, said mixture was filtered and washed with dimethylformamide. The obtained solid was dried at the temperature about 160° C. in the oven under reduced pressure for 24 hours. The metal organic frameworks were obtained.

Zirconium-Benzene Dicarboxylic Acid Adsorbent

The sample was prepared by the method described for the zirconium-benzene tricarboxylic acid adsorbent using 1,4-benzene dicarboxylic acid instead of 1,3,5-benzene tricarboxylic acid.

Copper-Benzene Tricarboxylic Acid Adsorbent Treated with Alcohol

The copper-benzene tricarboxylic acid adsorbent obtained from the above method was treated with methanol. The metal organic frameworks were immersed in methanol for about 18 hours. Then, said mixture was filtered and washed with methanol. The obtained solid was dried at the temperature about 120° C. under reduced pressure for 12 hours. The adsorbent treated with alcohol was obtained. Said treatment was performed using different amounts of alcohol which were 2.5 and 5 mole alcohol per gram of adsorbent weight.

Zirconium-Benzene Dicarboxylic Acid Adsorbent Treated with Alcohol

The sample was prepared by the method described above using zirconium-benzene dicarboxylic acid adsorbent instead of the copper-benzene tricarboxylic acid adsorbent. Said treatment was performed using different amounts of alcohol which were 2.5 mole alcohol per gram of adsorbent weight.

Test of Arsine Adsorption Performance

The test of arsine adsorption performance may be performed using the following conditions.

The adsorption of arsine from the hydrocarbon mixture was operated in the continuous adsorption column under gaseous condition using about 0.2 grams of the adsorbent. The adsorption process was operated at the temperature of 30° C., atmospheric pressure, and the gas hourly space velocity (GHSV) of about 30,000 mL $h^{-1}$ adsorbent $weight^{-1}$. The hydrocarbon mixture comprised propane, propylene, ethyl mercaptan, and arsine compounds. Then, the adsorption was monitored by measuring the remaining arsine compounds. The gas samples were randomly collected at the time wanted to be analyzed by UV spectrophotometry technique using silver diethyl thiocarbamate compound as the indicator.

In order to study the effect of type of the transition metal and type of the organic ligand in the metal organic frameworks on the arsine adsorption performance in hydrocarbon mixture having propane and propylene as the main components, the adsorbents prepared by different transition metal ions and organic ligands were studied using mole ratio of transition metal to the organic ligand of 2:1. The results were shown in FIG. 1.

Figure 2:
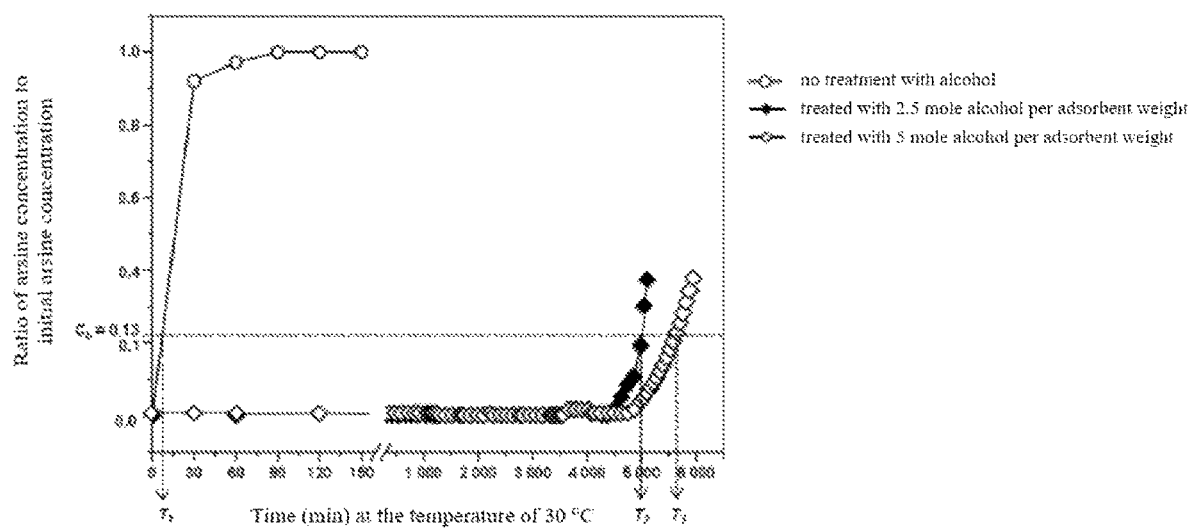
FIG. 2 shows the arsine separation performance of the metal organic frameworks comprising copper metal and 1,3,5-benzene tricarboxylic acid organic ligand treated with methanol solvent at different conditions.

In order to study the effect of the ratio of transition metal to organic ligand and the effect of the adsorbent treatment with alcohol, the adsorbents comprising different types and amounts of transition metal and organic ligand were tested for adsorption performances. The results were shown in table 1 and FIG. 2.

TABLE 1

Performance of the arsine separation from hydrocarbon mixture at the arsine concentration of 2 ppm by mole of different adsorbents

| Type of transition metal | Adsorbent Type of organic ligand | Mole ratio of transition metal to organic ligand | Amount of methanol to adsorbent weight (mole) | Adsorption amount (mg/g) |
|---|---|---|---|---|
| Copper | 1,3,5-benzene tricarboxylic acid | 1:1 | — | 0.63 |
|  |  | 2:1 | — | 4.14 |
|  |  | 3:1 | — | 5.36 |
| Copper | 1,4-benzene dicarboxylic acid | 2:1 | — | 9.98 |
| Zinc | 1,3,5-benzene tricarboxylic acid | 2:1 |  | 2.96 |
| Zinc | 1,4-benzene dicarboxylic acid | 2:1 |  | 1.76 |
| Zirconium | 1,3,5-benzene tricarboxylic acid | 2:1 |  | 1.42 |
| Zirconium | 1,4-benzene dicarboxylic acid | 2:1 |  | 35.6 |
| Copper | 1,3,5-benzene tricarboxylic acid | 2:1 | 2.5 | 2894 |
|  |  | 2:1 | 2.5 | 5204 |
| Zirconium | 1,4-benzene dicarboxylic acid | 2:1 | 5 | 16.6 |

From the results above, it can be said that the adsorbents according to the invention have high adsorption and separation performances of arsine as being stated in the objectives of this invention.

BEST MODE OR PREFERRED EMBODIMENT OF THE INVENTION

Best mode or preferred embodiment of the invention is as provided in the description of the invention.

The invention claimed is:

1. A process for removing arsine from a hydrocarbon mixture having 2 to 4 carbon atoms, comprising contacting the hydrocarbon mixture having 2 to 4 carbon atoms with an adsorbent, wherein said adsorbent is a metal organic frameworks (MOFs) comprising:
 a) at least 1 transition metal selected from a group 1B metal, and
 b) an organic ligand selected from a dicarboxylic acid compound or a tricarboxylic acid compound,
 wherein said adsorbent is subjected to treatment with alcohol prior to contacting the hydrocarbon mixture having 2 to 4 carbon atoms with the adsorbent.

2. The process according to claim 1, wherein the group 1B metal is selected from copper and silver.

3. The process according to claim 1, wherein the transition metal is copper.

4. The process according to claim 1, wherein the organic ligand is selected from 1,4-benzene dicarboxylic acid, 1,3,5-benzene tricarboxylic acid, 2,6-naphthalene dicarboxylic acid, and 1,2,4,5-benzene tetracarboxylic acid.

5. The process according to claim 4, wherein the organic ligand is 1,3,5-benzene tricarboxylic acid.

6. The process according to claim 1, wherein a mole ratio of the transition metal to the organic ligand is in a range of 1:1 to 3:1.

7. The process according to claim 6, wherein the mole ratio of the transition metal to the organic ligand is 2:1.

8. The process according to claim 1, wherein the alcohol is selected from methanol, ethanol, propanol, and butanol.

9. The process according to claim 8, wherein the alcohol is methanol.

10. The process according to claim 1, wherein said treatment with alcohol is operated by contacting the adsorbent with alcohol in an amount of 2 to 5 mole of alcohol per gram of the adsorbent weight.

11. The process according to claim 1, wherein the hydrocarbon having 2 to 4 carbon atoms is selected from ethane, propane, propylene, n-butane, and isobutane.

12. The process according to claim 1, wherein the hydrocarbon having 2 to 4 carbon atoms is propane and propylene.

13. The process according to claim 1, wherein the contacting the hydrocarbon mixture having 2 to 4 carbon atoms with an adsorbent is operated at a temperature in a range of 30 to 40° C. and a pressure in a range of 100 to 500 kPa.

* * * * *